(12) United States Patent
Choi

(10) Patent No.: US 10,401,396 B2
(45) Date of Patent: Sep. 3, 2019

(54) WEAKLY-BISTABLE SIGNAL DETECTORS HAVING ONE OR AN EVEN-NUMBER OF STAGES

(71) Applicant: Mee H. Choi, Sunnyvale, CA (US)

(72) Inventor: Mee H. Choi, Sunnyvale, CA (US)

( * ) Notice: Subject to any disclaimer, the term of this patent is extended or adjusted under 35 U.S.C. 154(b) by 371 days.

(21) Appl. No.: 14/645,275

(22) Filed: Mar. 11, 2015

(65) Prior Publication Data

US 2016/0266174 A1 Sep. 15, 2016

(51) Int. Cl.
| | |
|---|---|
| *A61B 5/04* | (2006.01) |
| *H03K 3/03* | (2006.01) |
| *G01R 19/00* | (2006.01) |
| *G01R 19/10* | (2006.01) |
| *G01R 21/12* | (2006.01) |
| *G01R 33/02* | (2006.01) |
| *H03L 7/099* | (2006.01) |

(52) U.S. Cl.
CPC ...... *G01R 19/0053* (2013.01); *A61B 5/04001* (2013.01); *A61B 5/04004* (2013.01); *G01R 19/0092* (2013.01); *G01R 21/12* (2013.01); *G01R 33/02* (2013.01); *H03K 3/0315* (2013.01); *H03L 7/0995* (2013.01); *G01R 19/10* (2013.01)

(58) Field of Classification Search
CPC .... G01R 20/12; G01R 33/02; G01R 19/0053; G01R 19/00532; H03K 3/0315; A61B 5/04001; H03L 7/0995

USPC ................ 324/457, 72; 331/52, 57
See application file for complete search history.

(56) References Cited

U.S. PATENT DOCUMENTS

| | | | | |
|---|---|---|---|---|
| 8,212,569 | B1* | 7/2012 | In ........................ | G01R 29/12 324/457 |
| 8,994,461 | B1* | 3/2015 | In ....................... | H03K 3/0322 331/44 |
| 2014/0364759 | A1* | 12/2014 | Choi .................. | A61B 5/04001 600/544 |
| 2015/0084704 | A1* | 3/2015 | In ....................... | H03K 3/0322 331/52 |
| 2016/0139190 | A1* | 5/2016 | Baglio ................. | G01R 29/12 324/457 |

* cited by examiner

*Primary Examiner* — Arnold M Kinkead
(74) *Attorney, Agent, or Firm* — Innovation Counsel LLP

(57) ABSTRACT

A method of detecting a relatively weak signal includes providing an oscillatory loop that can sustain oscillations, wherein the oscillatory loop has no more than one or an even-number of stages. The loop includes a first weakly bistable differential amplifier and a second weakly bistable differential amplifier. At least one of the first and second weakly bistable differential amplifiers is connected to a behavior perturbing coupling which is operative to introduce into the connected-to amplifier a behavior tipping signal where, even if the behavior tipping signal is much weaker than an oscillation of the one or multistage oscillatory loop, the relatively weak behavior tipping signal can nonetheless alter the oscillatory behavior of the multistage oscillatory loop in a distinguishable way. The system may be used for detecting outside a patient's body weak manifestations of internal nerve firings.

11 Claims, 17 Drawing Sheets

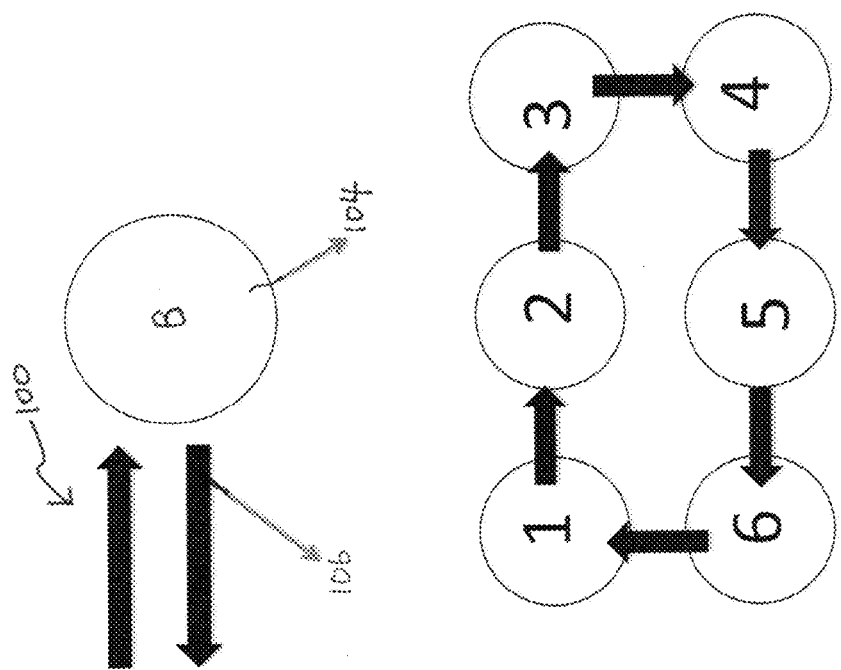
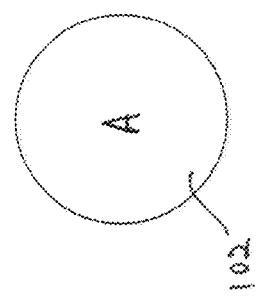
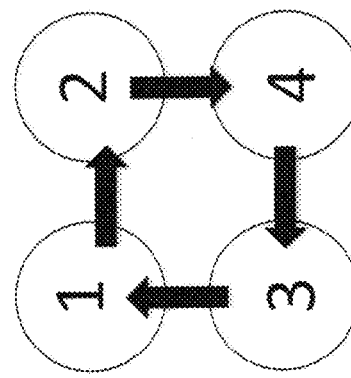
Fig. 1A
Fig. 1B
Fig. 1C

WEAKLY-BISTABLE SIGNAL DETECTORS HAVING ONE OR AN EVEN-NUMBER OF STAGES

FIELD OF DISCLOSURE

The present disclosure of invention relates generally to detection of analog signal events. The disclosure relates more specifically to detection of weak-magnitude analog signal events such as extracranial manifestations of intracranial neuron firings.

RELATED APPLICATIONS

U.S. patent application Ser. No. 13/912,900 filed on Jun. 7, 2013 by Mee H. CHOI et al. and which is originally entitled "Ultrasensitive and Compact Device for Noninvasive acquisition of Low Strength Bio Signals and Method of Using Same" is incorporated by reference herein.

RELATED TECHNOLOGY

Typically, when it is desirable to detect and measure analog signals, an analog amplifier is used where the amplifier has a relatively smooth (e.g., linear) and continuous transfer characteristic (e.g., output voltage over input voltage) over the input signal range of interest. The sensitivity of such smooth-continuum analog amplifiers may be limited, for example due to circuit components used to provide the relatively smooth (e.g., linear) and continuous transfer characteristic. Yet more specifically, when amplification components such as transistors are operated in the linear or saturated regions of their IV (current versus voltage) characteristic curves, they tend to have less sensitivity to minute input perturbations than when operated near their threshold nonlinear region of operation.

The inventive concept, at least in part, stems from the discovery that a relatively smooth (e.g., linear) and continuous transfer characteristic is not always necessary for signal detection and measurement. For example, signal detection and measurement may be performed in cases of sporadic analog events such as the extracranial manifestations of intracranial neuron firings, or other such non-continuous input events with weak signals.

In some instances it is desirable to simultaneously detect and/or measure a large number of noncontinuous and weak signal input events. This may be achieved by distributing extracranial signal collectors at many locations around a patient's skull (e.g., 10 or more such collectors). In some instances, it is desirable for the signal collecting devices to be low cost and/or disposable. Some signal collecting device designs that have active electronic circuits incorporated in them call for a large number of circuit stages. This requirement for a large number of circuit stages leads to the disadvantage of individual signal collection devices being relatively large, more prone to failure (due to internal complexity) and high in cost.

It is to be understood that this background of the technology section is intended to provide useful background for understanding the here disclosed technology and as such, the technology background section may include ideas, concepts or recognitions that were not part of what was known or appreciated by those skilled in the pertinent art prior to corresponding invention dates of subject matter disclosed herein.

SUMMARY

In one aspect, the inventive concept pertains to a signal sensing device that includes a first weakly bistable differential amplifier, a second weakly bistable differential amplifier, and a behavior perturbing coupling connected to at least one of the first and second weakly bistable differential amplifiers. The first weakly bistable differential amplifier is provided as a stage within an oscillatory loop configured to sustain oscillations, the oscillatory loop having no more than one stage of an even-number of stages. The second weakly bistable differential amplifier is provided also as a stage within the oscillatory loop. The behavior perturbing coupling may operate to introduce into the amplifier to which it is connected a behavior tipping signal where the behavior tipping signal alters the oscillatory behavior of the oscillatory loop in a distinguishable way. This may be true even if the behavior tipping signal is weaker than an oscillation of the oscillatory loop.

In another aspect, the inventive concept pertains to a method of detecting a weak signal by providing a multistage oscillatory loop configured to sustain oscillations. The loop includes, as at least one or two of its stages, first weakly bistable differential amplifier and a second weakly bistable differential amplifier where at least one of the first and second weakly bistable differential amplifiers is further connected to a behavior perturbing coupling that is operative to introduce into the amplifier to which it is connected a behavior tipping signal. Even if the behavior tipping signal is weaker than an oscillation of the oscillatory loop, the behavior tipping signal alters the oscillatory behavior of the oscillatory loop in a distinguishable way. The method also entails providing either the weak signal or a signal derived therefrom as the weak behavior tipping signal to the at least one of the first and second weakly bistable differential amplifiers.

Other aspects of the disclosure will become apparent from the below detailed description.

BRIEF DESCRIPTION OF THE DRAWINGS

The below detailed description section makes reference to the accompanying drawings, in which:

FIG. 1A is a diagram of a two-element intercoupled oscillatory system that may be operated in accordance with the present disclosure;

FIG. 1B is a diagram of a four-element intercoupled oscillatory system that may be operated in accordance with an embodiment of the disclosure;

FIG. 1C is a diagram of a six-element intercoupled oscillatory system that may be operated in accordance with an embodiment of the disclosure;

DETAILED DESCRIPTION

Figure 2:
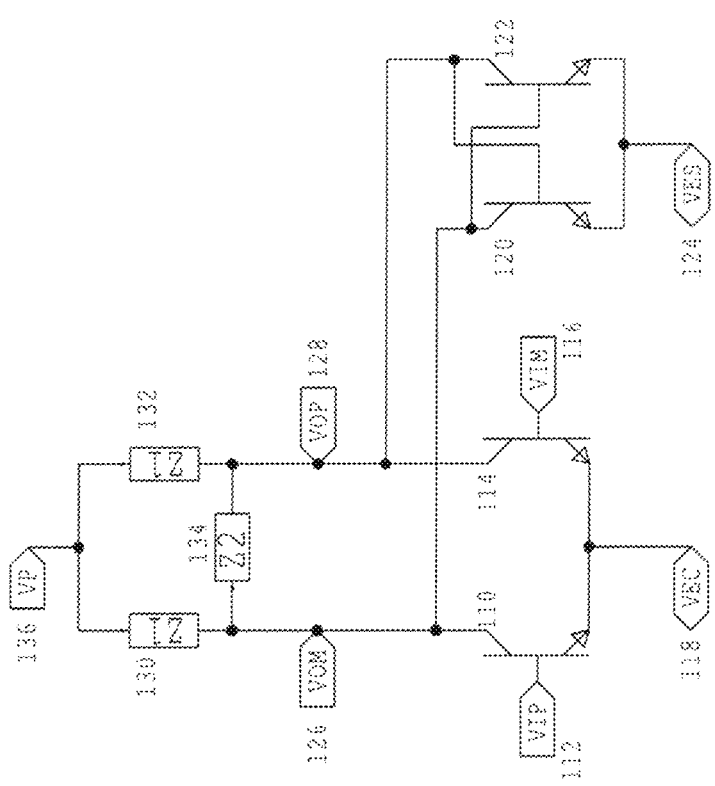
FIG. 2 is a schematic diagram showing a combined differential amplifier and weak bistable switch each implemented as a bipolar NPN differential-pair for controlling imbalanced current flow through generalized, current-splitting impedances.

Structures and methods may be provided in accordance with the present disclosure of invention for minimizing the cost, size and/or complexity of each weak signal collecting device.

One can aim that the signal collection units can be made smaller, more power efficient, and more reliable by reducing the number of circuit components at each signal collection location. In accordance with one aspect of the present disclosure, a two-stage system (a system with just two weakly bistable Voltage Controlled Oscillatory stages, a.k.a. wb-VCO stages, per collection location) is made possible. The two-stage system can be even further expanded into any even number stage system or can be further simplified to one-stage system.

FIG. 1A is a diagram of an oscillatory loop 100. The oscillatory loop 100 may detect and measure an input voltage or other weak-magnitude input signal (e.g., a low magnitude current). The particular embodiment that is depicted has two weakly-bistable Input Controlled Oscillatory stages 102, 104 (wb-ICO stages 102, 104 are respectively labeled as A and B). A cross-influencing, positive feedback coupling component 106 couples the two wb-ICOs 102, 104 to each other.

When no input signal (not shown) is applied to each of the wb-ICO's stages A and B, the combination of the two stages (102 and 104) and their cross-influencing coupling component 106 is such that one of two zero-input conditions is true: (1) the two wb-ICO stages, A and B, influence one another to be in an easily perturbed, first oscillating state; or (2) the two wb-ICO stages, A and B, influence one another to be not oscillating but additionally to be just outside of an easily perturbed-into (easily entered-into) second oscillating state. Then, when a weak magnitude input signal (e.g., voltage or current) is thereafter applied to each of the two wb-ICO stages (102 and 104), the two wb-ICO stages A and B influence one another to nonlinearly switch into an alternate state that is easily distinguishable from the original state. "Distinguishable" means the frequency of the oscillation changes (i.e. the frequency of an oscillation can change from 100 Hz to 0 Hz, or vice versa, making the oscillation appear or disappear.) More specifically, if the first zero-input condition (1) was true, then the application of the non-zero input signal would tip the two wb-ICO stages A and B out of the easily perturbed, first oscillating state and into either a nonoscillating state or a third oscillating state that is easily distinguishable from the first oscillating state. On the other hand, if the second zero-input condition (2) was true, then the application of the non-zero input signal would tip the two wb-ICO stages A and B out of their not-oscillating state and into their easily entered-into second oscillating state.

Figure 13:
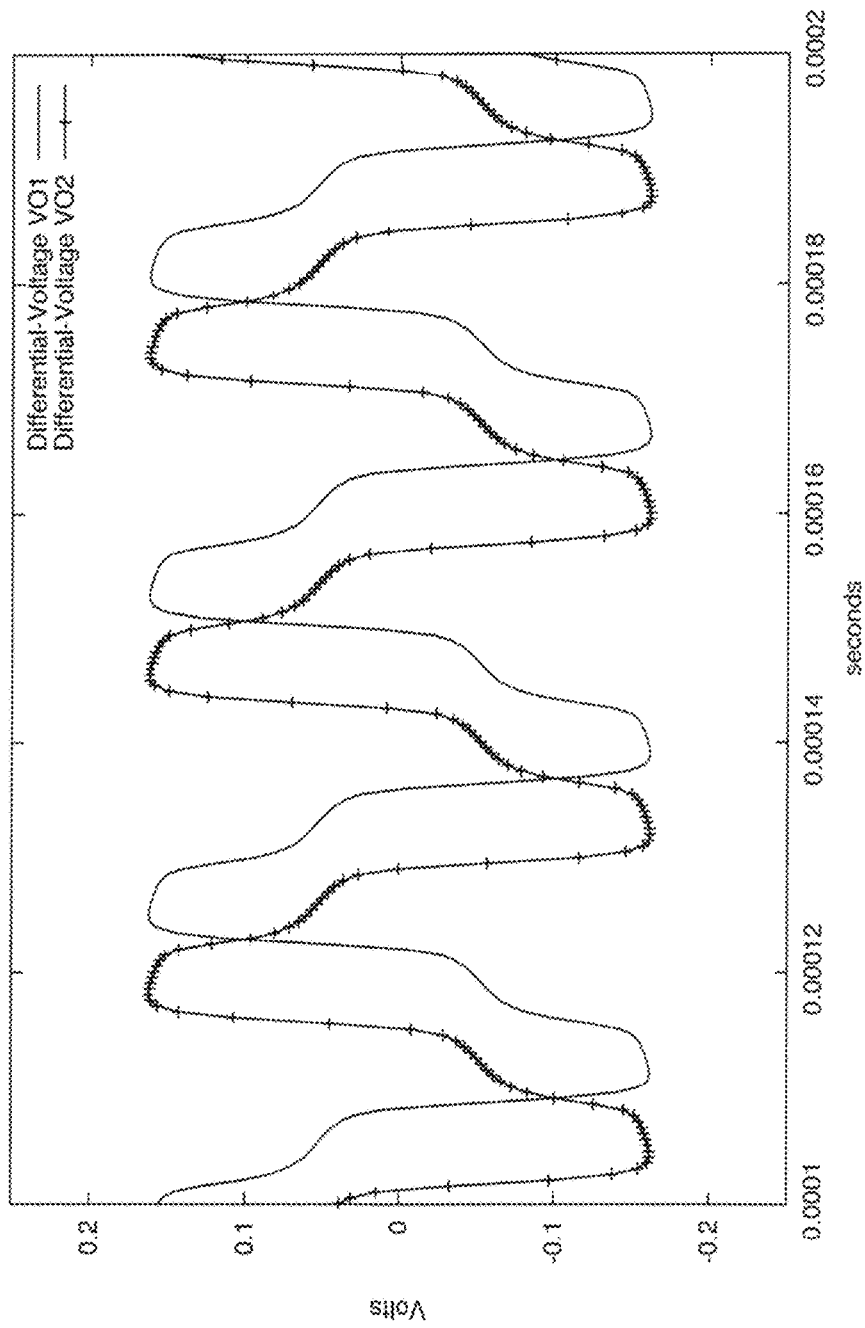
FIG. 13 is a plot produced from an HSPICE simulation result showing the differential output voltages for the two weakly bistable element system.
Figure 14:
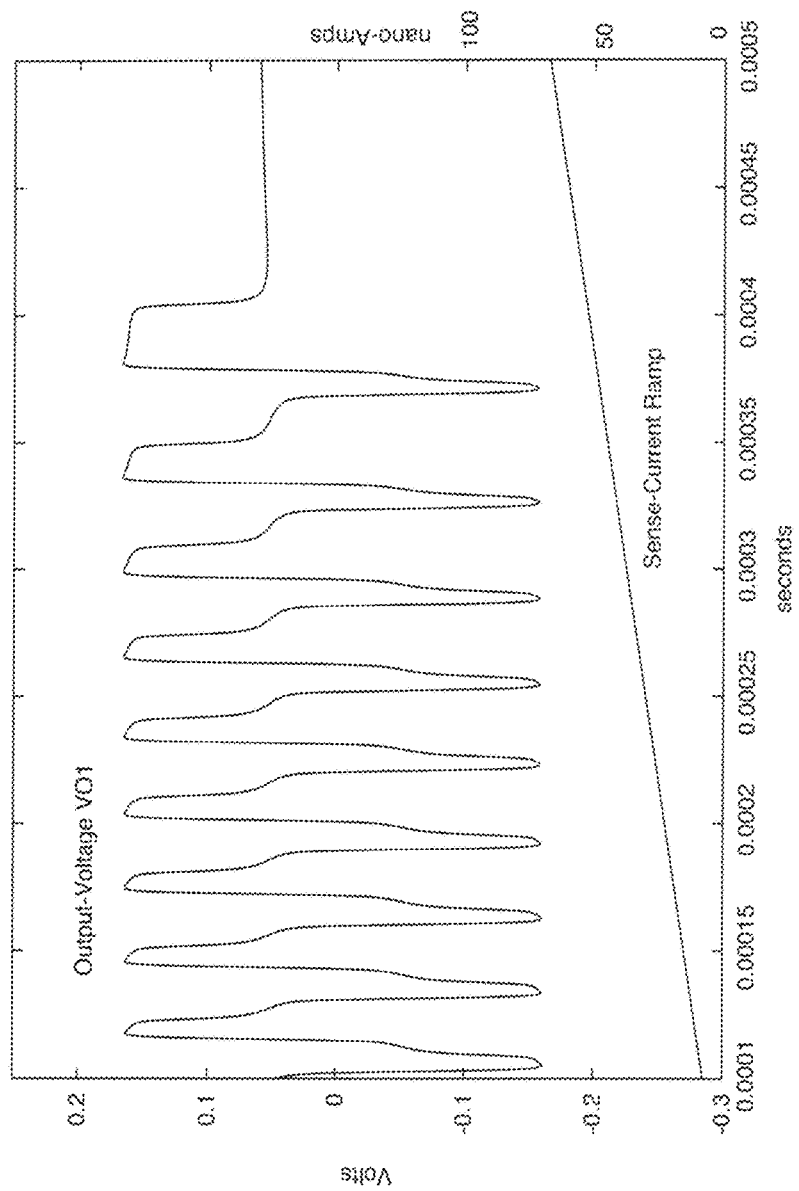
FIG. 14 is a plot produced from an HSPICE simulation result showing the differential output voltages when a behavior-tipping and weak sense current is applied as an increasing ramp over time.

While the above and relatively generalized introduction may appear somewhat abstract, a brief look at the plots of FIGS. 13 and 14 will clarify what a first oscillating state (FIG. 13) might look like and what easily distinguishable other oscillating states and/or a non-oscillating state (FIG. 14) might look like.

FIG. 2 depicts one implementation of the wb-ICO stages shown in FIG. 1A, FIG. 1B, and FIG. 1C. The below circuit descriptions assume a level of skill of a trained electrical engineer who designs mixed signal, analog and digital integrated circuits (monolithically integrated circuits) where the concepts of circuit blocks or cells are well understood, by such a skilled person as are the concepts of circuit elements, circuit branches, voltage nodes, and simple network theory. Additionally, the fundamental characteristics of capacitors, resistors, NPN bipolar transistors, PNP bipolar transistors, NMOS, and PMOS circuit should be familiar to such an artisan. In addition, terms such as positive, negative, non-inverting, inverting, S-plane or Laplace transform and the like, should be familiar to such a person.

Accordingly, FIG. 2 will be understood to be an example of an NPN bipolar differential-pair realization of one (e.g., A) of the two wb-ICO stages, A and B of FIG. 1A. Although not explicitly shown, the other stage (e.g., B) of the two wb-ICO stages has the same design and where the input signal is of a weak magnitude, behavior-tipping input signal can be a differential voltage signal or a differential current signal applied at nodes 112 and 116. A behavior-tipping input signal of a weak magnitude has a current of a magnitude less than 100 nA. In some embodiments, the weak behavior-tipping signal has a magnitude less than 25 nA. In designing a weakly-bistable oscillatory system such as that of FIG. 1A, the one stage portion shown in FIG. 2 may be used as a single stage of a multi-stage weakly-bistable VCO or ICO. In FIG. 2, a first NPN transistor 110 and a second NPN transistor 114 (where 110 and 114 may be monolithically integrated replicas of one another) are connected to form a differential, current splitting pair. As used in reference to FIG. 2-FIG. 16, "connected" means electrically connected, either directly or with intervening elements. The emitter of NPN 110 connects to the emitter of NPN 114 to define a common-emitter node VEC 118. The collector of NPN 110 connects to one end of impedance Z1 130 and impedance Z2 134 to define a respective first (minus) output node VOM 126. The impedances 130, 132, and 134 are part of "a differential load portion," and they are connected to a "first current-splitting node" 136. The collector of NPN 114 connects to one end of another and identical impedance Z1' 132 and to the other end of impedance Z2 134 to form the second (positive) output-node VOP 128. The other ends of impedance Z1 130 and of impedance Z1' 132 connect together at a power rail voltage node VP 136. In this diagram third NPN transistor 120 and fourth NPN transistor 122 also form a differential current splitting pair except that they are not driven by the differential input voltage signal applied at nodes 112 and 116. Nodes 112 and 116 are herein referred to as "a differential amplifier portion." Instead, the base of NPN 120 connects to the collector of NPN 122 and similarly, the base of NPN 122 connects to the collector of NPN 120. NPN 120 and NPN 122 are herein referred to as "a latch portion." Additionally, the emitter of NPN 120 connects to the emitter of NPN 122 to form the common-emitter node VES 124. The collector of NPN 120 also connects to output-node VOM 126 while the collector of NPN 122 also connects to output-node VOP 128. The base of NPN 110 is the positive (non-inverting) input node VIP 112 while the base of NPN 114 is the minus (inverting) input node VIM 116. It is to be understood that the illustrated circuit is preferably all fabricated on a single monolithically integrated circuit chip such that the differential current splitting components are essentially identical. While in each differential pair of NPN transistors, the respective current splitting transistors (e.g., 112 and 116) should be of the same size as each other (e.g., same PN junction widths and/or lengths), it is within the contemplation of the present disclosure that the other pair (e.g., 120 and 122) may be constituted by same but smaller or larger such NPN transistors. In one embodiment, transistors 120 and 122 are smaller than corresponding NPN transistors 112 and 116.

Those skilled in the art will appreciate from FIG. 2 that within each such wb-VCO or wb-ICO stage there are two current splitting functions present, a first due to how the differential input signal VIP-VIM tips the first and second transistors (110 and 114) out of balance and a second due to how the third and fourth transistors (122 and 120) tip the differential output signal VOP-VOM out of balance.

As briefly mentioned above, it is possible to operate at least the pair of differential amplifier transistors 110 and 114 in the nonlinear and near threshold region of operation such that even small perturbations in the differential input currents that enter the base terminals of NPN transistors 110 and 114 will create a greatly amplified difference at the corresponding output nodes (126 and 128) because one of the so-perturbed transistors is urged closer to, or over its threshold point while the other is urged below or further below its respective threshold point. In other words, by operating in the low current, nonlinear regions of the IV curves of at least the differential amplifier transistors pair, 110 and 114, a relatively high degree of sensitivity to even small perturbations in input current (base currents of 110 and 114) may be obtained. Operation in the low current, nonlinear regions may be established by appropriately controlling the sink current (common tail current) drawn out of the VEC node 118. The VEC node 118 is herein also referred to as "an amplifier biasing portion."

When considered alone, the differential amplifier formed by NPN transistors 110 and 114 can be thought of as a highly sensitive playground swing that can easily be tipped from a perfectly balanced state to an imbalanced state by application of a weak magnitude tipping force. On the other hand, when the weak bistable latch circuit of NPN transistors 120 and 122 is added, a degree of bi-stability is imparted onto the wb-ICO stage. The amount of added bi-stability can be controlled by appropriately adjusting the sink current (common tail current) drawn out of the VES node 124. The VES node 124 is herein referred to as "a latch biasing portion." When the current through the VES node 124 is zero, the bistable latch NPN transistors 120 and 122 do not bleed any currents out of the impedance branches (130, 132) of the differential amplifier and thus do not impart a degree of bi-stability to it. When the current flowing out through the VES node 124 is relatively small, the bistable latch NPN transistors 120 and 122 can be caused to operate in their near-threshold states whereby even small perturbations of output voltage between nodes 128 (VOP) and 126 (VOM) can switch the weakly bistable latch circuit (120 and 122) from one bistable state to an opposed bistable state.

Figure 3:
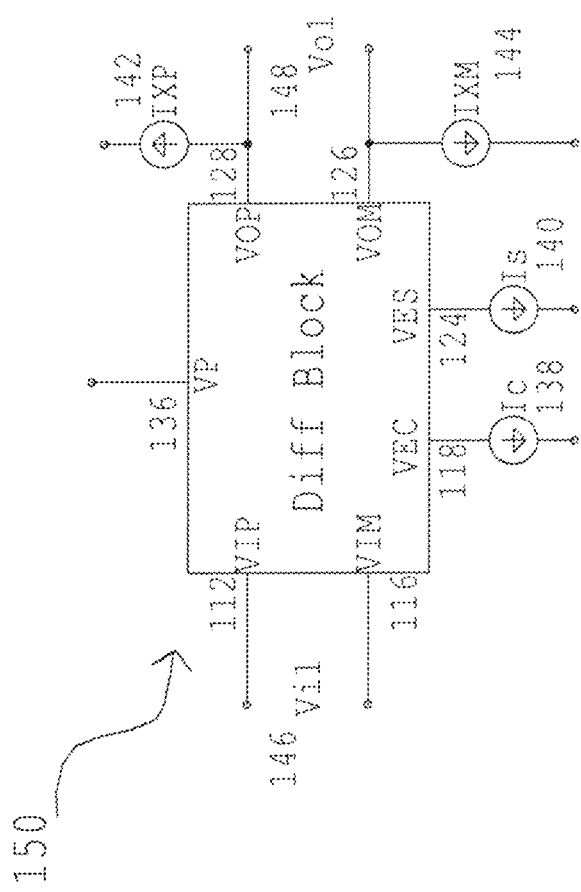
FIG. 3 is a block diagram representation of a weakly bistable element block with control and tail currents.

FIG. 3 schematically represents the circuitry of FIG. 2 as a weakly bistable (wb) differential circuit block 150 having input nodes VIP (112) and VIM (116); output nodes VoP (128) and VoM (126); power voltage node VP (136) and current conducting branches IC (138), IS (140), IXP (142) and IXM (144). Current conducting branches IC (138) and IS (140) respectively emanate from common emitter nodes VEC (118) and VES (124). Current conducting branches IXP (142) and IXM (144) respectively emanate from output nodes VOP (128) and VOM (126). In one embodiment, the branched-off currents, IXP (142) and IXM (144) that are bled off from their respective current conducting branches, operate as oscillatory-state altering currents.

For sake of completeness, the labeling in FIG. 3 names the voltage difference between input nodes VIP 112 and VIM 116 as the differential input signal Vi1 146. Similarly, it names the voltage difference between output nodes VOP 128 and VOM 126 as differential output signal Vo1 148. By convention, the differential signal Vi1 146 represents VIP 112 minus VIM 116, and the differential signal Vo1 148 represents VOP 128 minus VOM 126.

In one embodiment, the magnitudes of each of the IC (138) and IS (140) branch currents are respectively controlled by respective current sourcing circuits (e.g., constant current sourcing circuits). In one embodiment, the magnitudes of each of the IXP (142) and IXM (144) branch currents are respectively controlled by respective, but at the same time variable current sourcing circuits (in other words, not constant current sourcing circuits). In one embodiment, the so-called, external tail currents that are drawn out of current conducting branches IXP (142) and IXM (144) are determined by an attached (not shown) sensing interface circuit. (See briefly FIG. 7 which is detailed later below.)

In one embodiment, the head current entering into top node 136 is provided by a constant voltage source, VP.

In one embodiment, the weakly bistable differential amplifier stage (150) depicted in FIG. 3 is replicated so as to define an even number (two or more) of such stages on a monolithically integrated circuit chip. The illustrated connections can give the following set of analysis equations 152 which relate nonlinear Ebers Moll terms (on the right sides of the equations) with the Laplace transform L(−1) or the complex impedance terms "s" (on the left side).

$$L^{-1}(V_d/Z_n) = I_c \times \tan h(V_{i1}) - I_s \times \tan h(V_{o1}) - I_x$$

$$V_{o1} = VOP - VOM$$

$$V_{i1} = VIP - VIM$$

$$I_x = IXP - IXM$$

$1/Z_n = 1/Z_1 + 2/Z_2$ is a complex impedance expressed in "s"

A more detailed Ebers Moll derivation is also provided in U.S. Pat. No. 8,212,569 B1.

Figure 4:
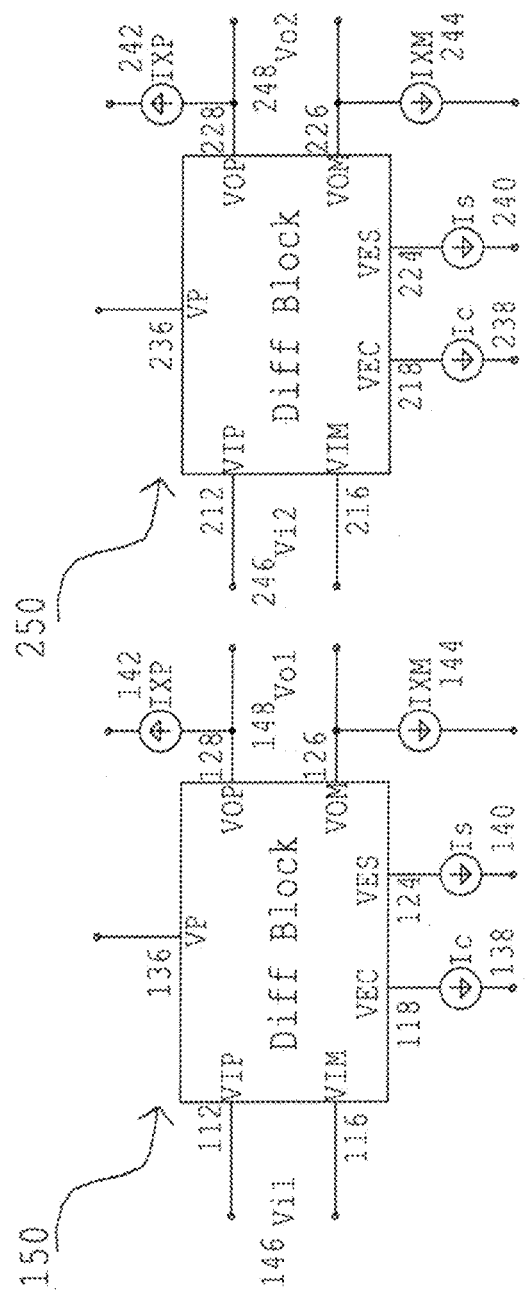
FIG. 4 is a block diagram representation showing two weakly bistable elements with control and tail currents.

FIG. 4 shows a monolithically integrated circuit having two identical weakly bistable element stages formed thereon: stage 150 and stage 250. Both stages are configured to be biased with identical VEC and VES tail current biases as well as same head end VP (136, 236) power voltages. Moreover, the minus side output bleeder currents IXM 144 and 244 are identical and the positive side output bleeder currents IXP 142 and 242 are identical. Therefore, as indicated by the following set of equations 252, it is possible to derive a set of circuit block equations relating the nonlinear Ebers Moll terms (on the right) with the Laplace transform L(−1) of the complex impedance term in "s" (on the left).

$$L^{-1}(V_o/Z_n) = I_c \times \tan h(V_i) - I_s \times \tan h(V_{out}) - I_x$$

$$V_{out} = VOP - VOM$$

$$V_i = VIP - VIM$$

$$I_x = IXP - IXM$$

$1/Z_n = 1/Z_1 + 2/Z_2$ is a complex impedance expressed in "s"

In the case of the second stage 250 in FIG. 4, the differential input voltage is denoted as Vi2 (246) and the differential output voltage is denoted as Vo2 (248).

The wb-differential circuit block 150 is herein also referred to as "a first weakly bistable differential amplifier." Where there are two stages, as in FIG. 4, the second stage 250 may herein be referred to as "a second weakly bistable differential amplifier." The positive coupling component 106 may herein be referred to as "a behavior perturbing coupling."

Figure 5:
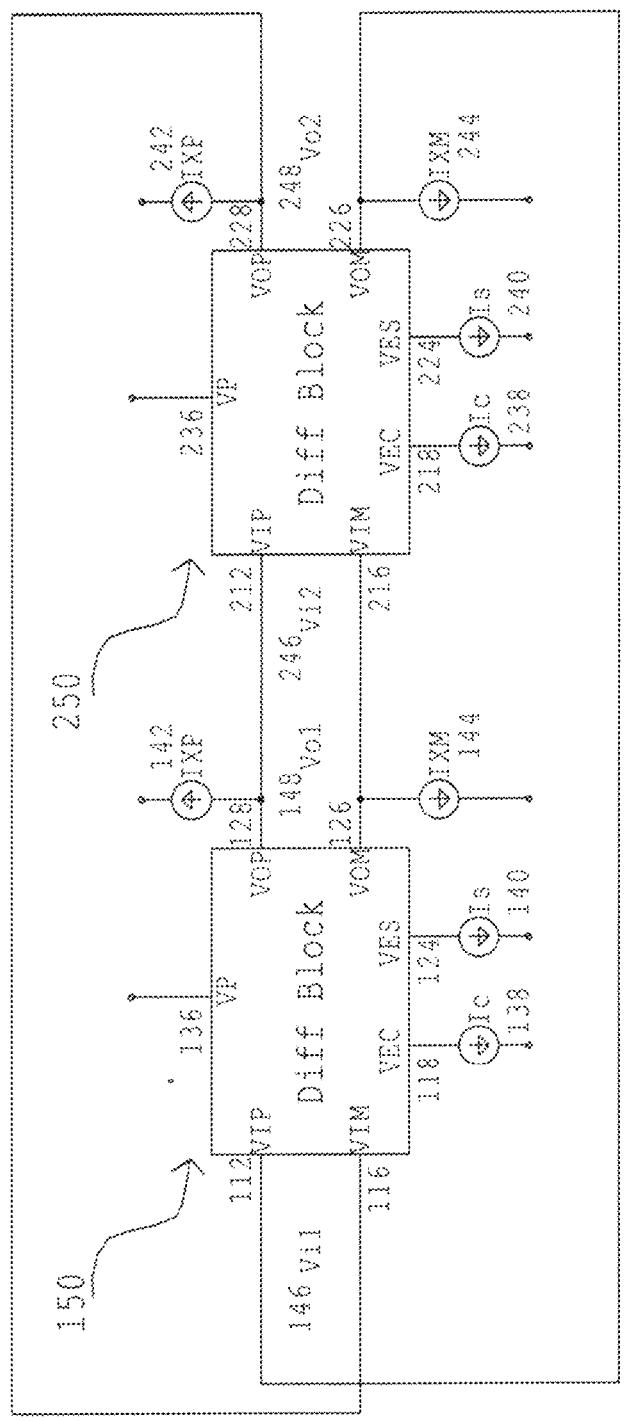
FIG. 5 shows a connection methodology for two weakly bistable elements.

FIG. 5 shows a substantially same monolithically integrated circuit as FIG. 4 but an interstage coupling component 106 is provided such that Vi2=Vo1 and Vi1=−Vo2. The positive feedback coupling component 106 shown in FIG. 1 corresponds to a combination of elements 126, 128, 212, and 216. An inversion function (times negative one) is included in the feedback coupling from the second stage 250 to the first stage 150. This interstage coupling is summarized in the equation set 254 shown below:

$$Vi1 = -Vo2$$

$$Vi2 = +Vo1$$

More specifically, node VIP 112 of stage element 150 is connected to node VOM 226 of stage element 250; while node VIM 116 of stage element 150 is connected to node VOP 228 of stage element 250. This causes the condition Vi1 146 to be equal to the negative of Vo2 248. Also, node VOP 128 of stage element 150 is connected directly to node VIP 212 of stage element 250; while node VOM 126 of stage element 150 is connected directly to node VIM 216 of stage element 250. This causes the condition Vi2 246 to be equal to Vo1 148.

It should be noted that the variable bleeder current IXM 144 can be seen as perturbing the input current that feeds the base of the NPN transistor inside of stage 250 and coupled to minus node VIM 216. Similarly, the variable bleeder current IXM 244 can be seen as perturbing the input current that feeds the base of the NPN transistor inside of stage 150 and coupled to positive node VIP 112. Additionally, the variable bleeder current IXP 142 can be seen as perturbing the input current that feed the base of the NPN transistor inside of stage 250 and coupled to positive node VIP 212. Similarly, the variable bleeder current IXP 242 can be seen as perturbing the input current that feed the base of the NPN transistor inside of stage 150 and coupled to minus node VIN 116. Because the respective NPN transistors inside stage 150 and 250 are being biased to be within or close to their respective nonlinear operation regions (e.g., subthreshold), they are very sensitive to even the smallest of changes in their respective bleeder currents: IXM's 144 and 244 and IXP's 142 and 242. Thus these bleeder currents may be used as inputs for controlling the behavior of the negative feedback wise coupled pair of weakly bistable differential amplifier stages 150 and 250.

In one embodiment of the monolithically integrated circuit shown in FIG. 5, if the output voltages Vo1 and Vo2 are initially preset to zero and all the bleeder currents (IXM's 144 and 244 and IXP's 142 and 242) are initially preset to zero and the Is bistability-adding currents (140 and 240) are sufficiently high, then the feedback-wise coupled system will remain essentially balanced. Then even a very minute perturbation (e.g., in the nanoAmpere range) of the bleeder currents (IXM's 144 and 244 and IXP's 142 and 242) will tip the feedback-wise coupled system into an easily detected oscillatory mode. Accordingly, the illustrated circuit (FIG. 5) may be used to detect the occurrence of a very small signal change where that signal change is introduced within one or more of the bleeder currents (IXM's 144 and 244 and IXP's 142 and 242). For example the very small signal change may be that induced outside of a health patient's body (supra-cutaneously) by one or more nerve cells (e.g., intra-cranial nerve cells) firing inside the patient's body. After the weak signal firing is detected by observing the transition of the two-stage system (150-250) from an oscillatory mode to a non-oscillatory mode in which detuning of the frequency of the oscillation occurs. This detuning of the oscillation can be automatically recorded and the degree in which the detuning occurs depends on the strength of the input signal. In other words, the circuit is tuned to an oscillatory mode where the residence time distribution (duty cycle) changes, and a signal that is outside the operating range of the tuned circuit (e.g., too strong) will induce a non-oscillatory mode. When the input signal disappears, the two-stage system can be automatically be reset to await the next detection of the weak signal event. In one embodiment, the illustrated two-stage system (150-250) is incorporated into a weak signal collection device that is attached adhesively or otherwise to the patient's skin at a desired location on the body.

Figure 6:
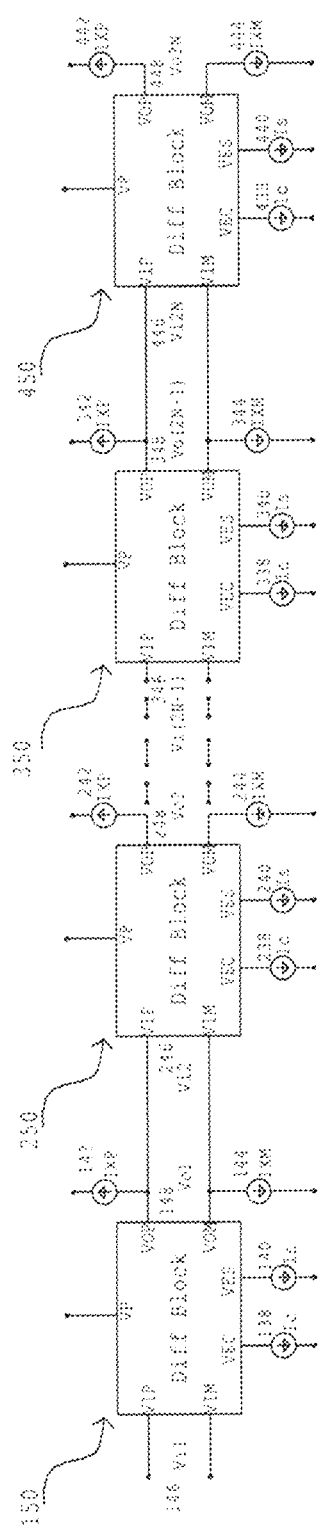
FIG. 6 shows a generalized connection methodology for an even number of 2N weakly bistable elements.

FIG. 6 shows a generalized multi-stage feedback system that may be operated in accordance with the present teachings. An even number of cascaded circuit stages 2N is provided, where N represents an arbitrary whole number (1, 2, 3, . . . ). In the drawing, only the first two stages, stage 150 and stage 250, and the final two stages, stage 350 and stage 450 are shown for the case of N equal to or greater than 2. The stages are designed to be equivalent with equivalent currents and equivalent biases. Each stage has elements, voltages, and currents which are equivalent in concept and design to those of FIG. 3. The concepts of FIG. 4 and FIG. 5 are generalized with the understanding that the notations of FIG. 3 apply and with the idea that all stages are replicas. Therefore, stage 350 also represents a "Diff Block" composed of the elements of FIG. 2 with respective and independent labels to distinguish it from other stages. Again using the two-port electrical engineering convention, the element stage is drawn with its input nodes VIP and VIM on the left and the output nodes VOP and VOM on the right. This two port representation shows differential input signal Vi(2N−1) 346 and differential output signal Vo(2N−1) 348. Again by convention the differential signal Vi(2N−1) 346 represents VIP minus VIM, and the differential signal Vo(2N−1) 348 represents VOP minus VOM. In this schematic, the additional current source Ic 338 provides another tail current of value Ic. The additional current source Is 340 provides another tail current of value Is. The additional bleeder currents (which can be controlled by corresponding current sources) IXP 342 and IXM 344 are control currents that in one embodiment (see FIG. 7), are derived from a sensing interface circuit. Moreover, stage 450 also represents a "Diff Block" composed of the elements of FIG. 2 with independent labels to distinguish it from other stages. Using two-port electrical engineering convention, the element stage is drawn with its input nodes VIP and VIM on the left and the output nodes VOP and VOM on the right. This two port representation shows differential input signal Vi(2N) 446 and differential output signal Vo(2N) 448. Again by convention the differential signal Vi(2N) 446 represents VIP minus VIM, and the differential signal Vo(2N) 448 represents VOP minus VOM. In this schematic the additional current source Ic 438 provides another tail current of value Ic. The additional current source Is 440 provides another tail current of value Is. The additional current sources IXP 442 and IXM 444 are control currents which can be derived from a sensing interface circuit. These 2N stages are also connected in a negative-feedback configuration suitable for creating oscillations. The connection concept is summarized in equations below:

$$Vi1 = -VoN$$

$$Vi(k+1) = +Vok \text{ for } k=1,2,3, \ldots N-1$$

The differential input Vi1 146 is connected so as to equal to the negative of the differential output Vo(2N) 448, while the remainder of the differential inputs Vi(k+1) are connected so as to be equal to the respectively preceding differential outputs Vo(k) for k=1, 2, . . . (N−1).

Figure 7:
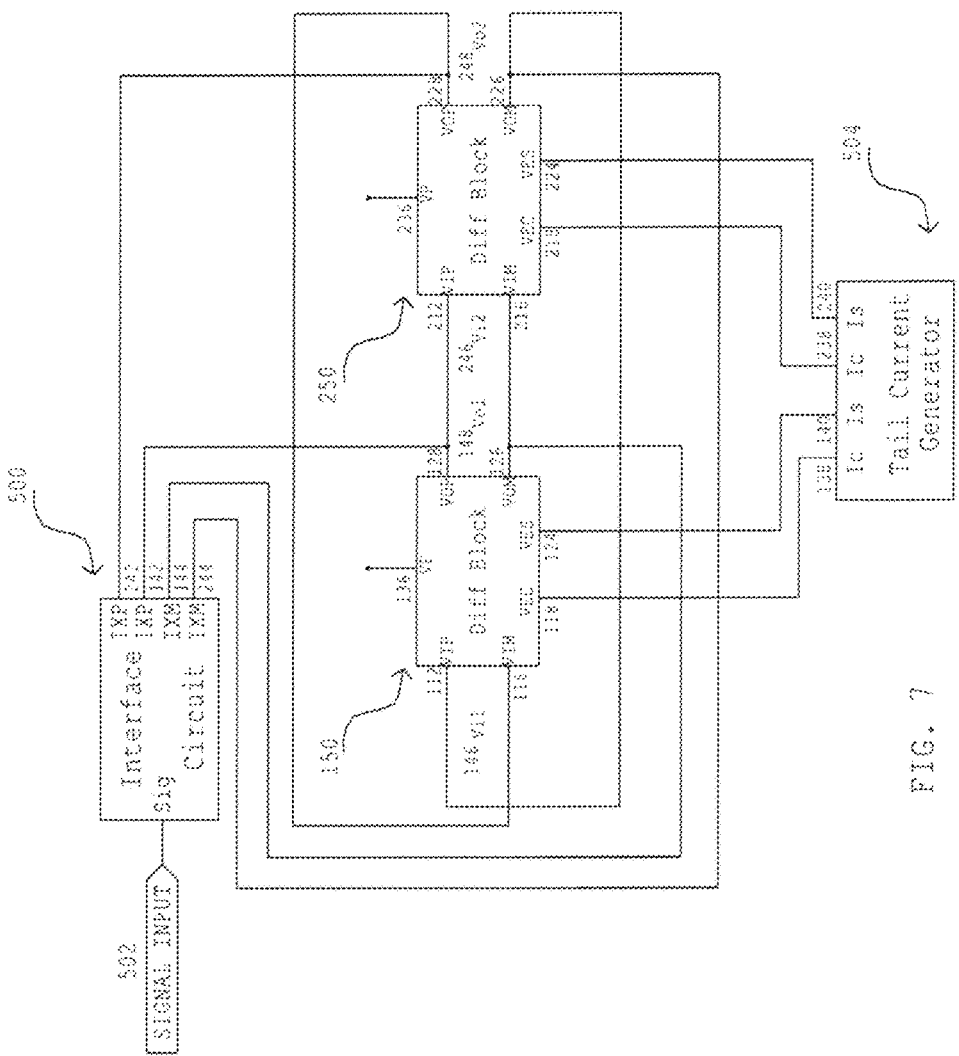
FIG. 7 is a circuit-block realization of the two element system showing tail-current and sense current blocks.

FIG. 7 illustrates one possible way in which the two-stage weakly bistable system can be coupled and driven for sensing an external voltage signal (input signal) 502. In this diagram the control currents are provided from the sense interface circuit block 500, and the tail currents are controlled by a tail currents generator block 504. The purpose of the sense interface circuit block 500, referred to as the "Interface Circuit", is to convert the to-be-sensed voltage signal 502 into appropriate control currents IXP and/or IXM. Here the connections are as follows: the sense signal, either a voltage or a current signal, is detected at signal input port 502; control current IXP 142 of the interface circuit block 500 connects to node VOP 128 of stage 150"; control current IXP 242 of the interface circuit block 500 connects to node VOP 228 of stage 250; control current IXM 144 of the interface circuit block 500 connects to node VOM 126 of stage 150; control current IXM 244 of interface circuit block 500 connects to node VOP 226 of stage 250.

The purpose of circuit block 504, referred to as a "Tail Current Generator", is to provide respective tail currents of value Ic and of value Is to each of the stages. Here the connections are as follows: circuit block 504 tail current Ic 138 connects to node VEC 118 of stage 150"; circuit block 504 tail current Is 140 connects to node VES 124 of stage 150; circuit block 504 tail current Ic 238 connects to node VEC 218 stage 250; circuit block 504 tail current Is 240 connects to node VES 224 of stage 250.

Figure 8:
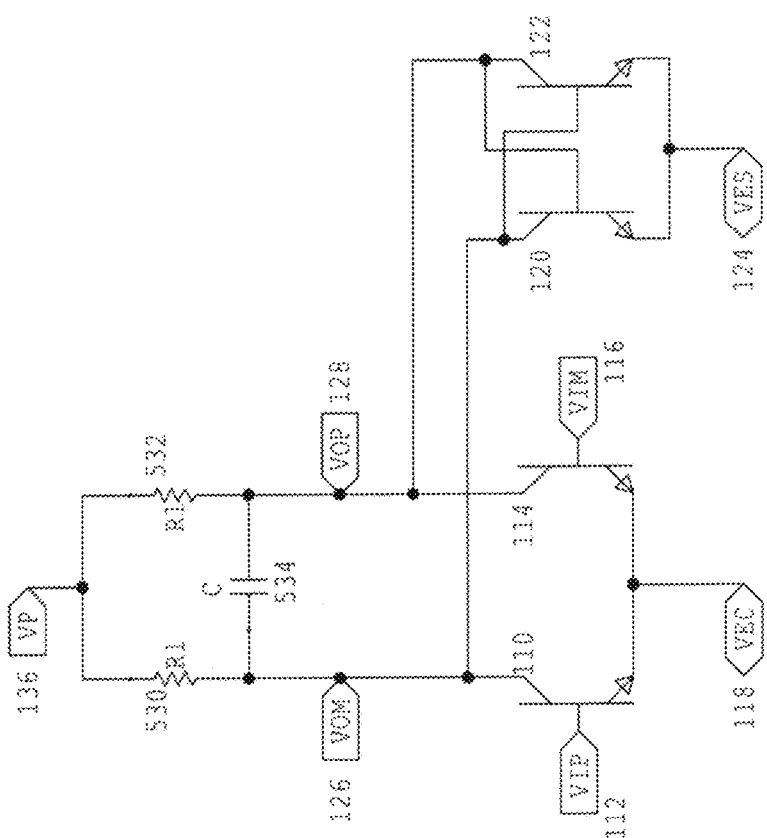
FIG. 8 shows a bipolar NPN differential-pair realization of a weakly bistable element block with a passive RC differential load.

FIG. 8 shows an embodiment of the circuit stage of FIG. 2. In this embodiment the element Z1 130 is a resistor R1 530, and the element Z1 132 is an identical and monolithically integrated resistor R1 532. Also, the element Z2 134 is a capacitor C 534 that may be monolithically integrated on the same circuit chip. The capacitor C 534 provides AC coupling between the VOP and VOM nodes (128 and 126). The capacitance of capacitor C 534 may be varied as appropriate for the desired oscillatory behaviors of the system.

Figure 9:
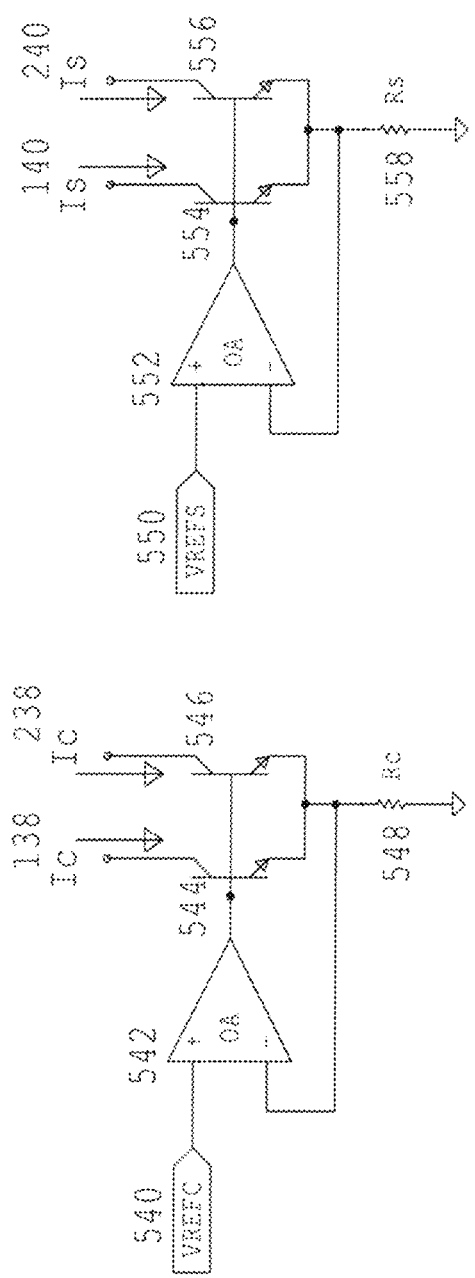
FIG. 9 shows an active-current source circuit for creating matched tail currents.

FIG. 9 shows a circuit technique for creating the tail current generator block 504 of FIG. 7. In this circuit embodiment the tail currents Ic 138 and Ic 238 are created from the active current source comprised of operational amplifier OA 542, NPN 544, NPN 546, resistor Rc 548, and voltage reference signal VREFC 540. The voltage signal VREFC 540 connects to the noninverting (plus) terminal of OA 542. The base of NPN 544 and of NPN 546 connect to the output of OA 542. One end of resistor Rc 548 connects to the emitter of NPN 544, the emitter of NPN 546, and the inverting input (minus) terminal of OA 542. The other end of resistor Rc 548 connects to ground. This embodiment shows the technique for creating two equal tail currents Ic 138 and Ic 238, and this technique may be generalized to create any number of equal tail currents by adding additional transistors in parallel. The illustrated circuit components may be monolithically integrated on the same chip as that of the multi-stage weakly-bistable oscillatory system (e.g., 150, 250, . . . ).

In a similar manner, in FIG. 9, the tail currents Is 140 and Is 240 are created from the active current source comprised of operational amplifier OA 552, NPN 554, NPN 556, resistor Rs 558, and voltage reference signal VREFS 550. The voltage signal VREFS 550 connects to the non-inverting (plus) terminal of OA 552. The base of NPN 554 and of NPN 556 connect to the output of OA 552. One end of resistor Rs 558 connects to the emitter of NPN 554, the emitter of NPN 556, and the inverting input (minus) terminal of OA 552. The other end of resistor Rs 558 connects to ground. This embodiment shows the technique for creating two equal tail currents Is 140 and Is 240, and this technique may also be generalized to create any number of equal tail currents by adding additional transistors in parallel.

Figure 10:
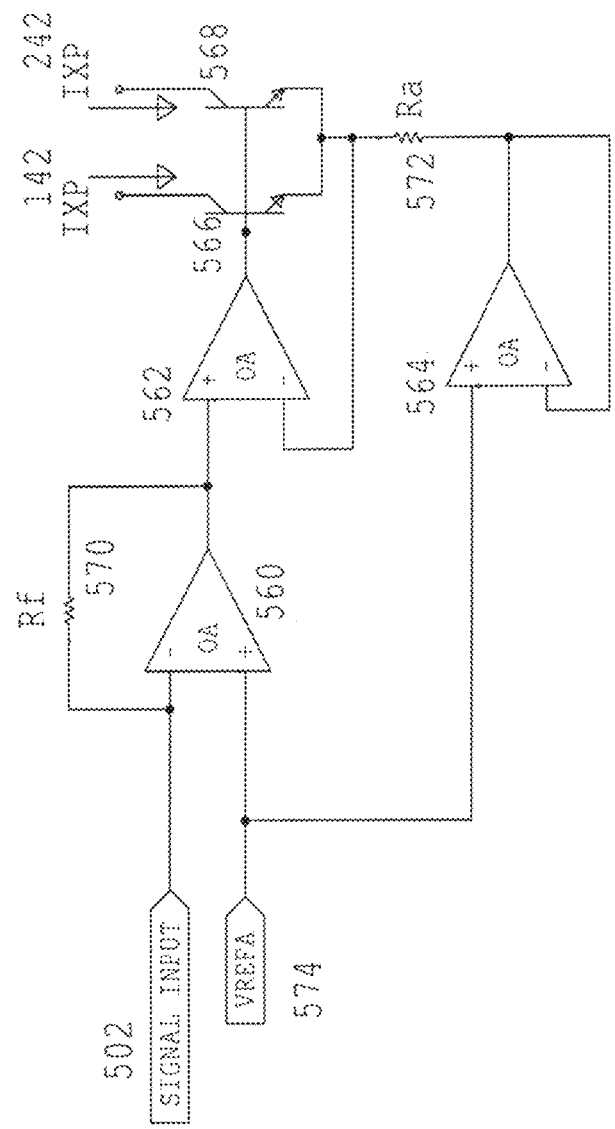
FIG. 10 shows an operational amplifier realization of a sense-current multiplier for generating matched control currents.

FIG. 10 shows a circuit technique for creating the interface circuit block 500 of FIG. 7. In this circuit embodiment only the control currents IXP 142 and IXP 242 are created as a single ended embodiment of circuit block 500. In addition, the sense signal input 502 is a current signal. In this embodiment control current IXP 142 is the collector current of NPN 566, and control current IXP 242 is the collector current of NPN 568. Also there are three operational amplifiers OA 560, OA 562, and OA 564. There is a fixed voltage reference VREFA 574, and there are two resistors Rf 570 and Ra 572. Operational amplifier OA 560 is connected with shunt feedback resistor Rf 570 so that the signal input 502 connects to the inverting (minus) input of OA 560 and to one end of Rf 570. The other end of Rf 570 connects to the output of OA 560 and to the non-inverting (plus) input of OA 562. The voltage reference VREFA 574 connects to the non-inverting (plus) inputs of OA 560 and OA 564. The inverting (minus) input of OA 564 connects to the output of OA 564 and to one end of resistor Ra 572. The other end of Ra 572 connects to the emitter of NPN 566, the emitter of NPN 568, and to the inverting input of OA 562. The output of OA 562 connects to the base of NPN 566 and NPN 568. This embodiment shows the technique for creating two equal control currents IXP 142 and IXP 242 and may also be generalized to create any number of equal tail currents by adding additional transistors in parallel.

Figure 11:
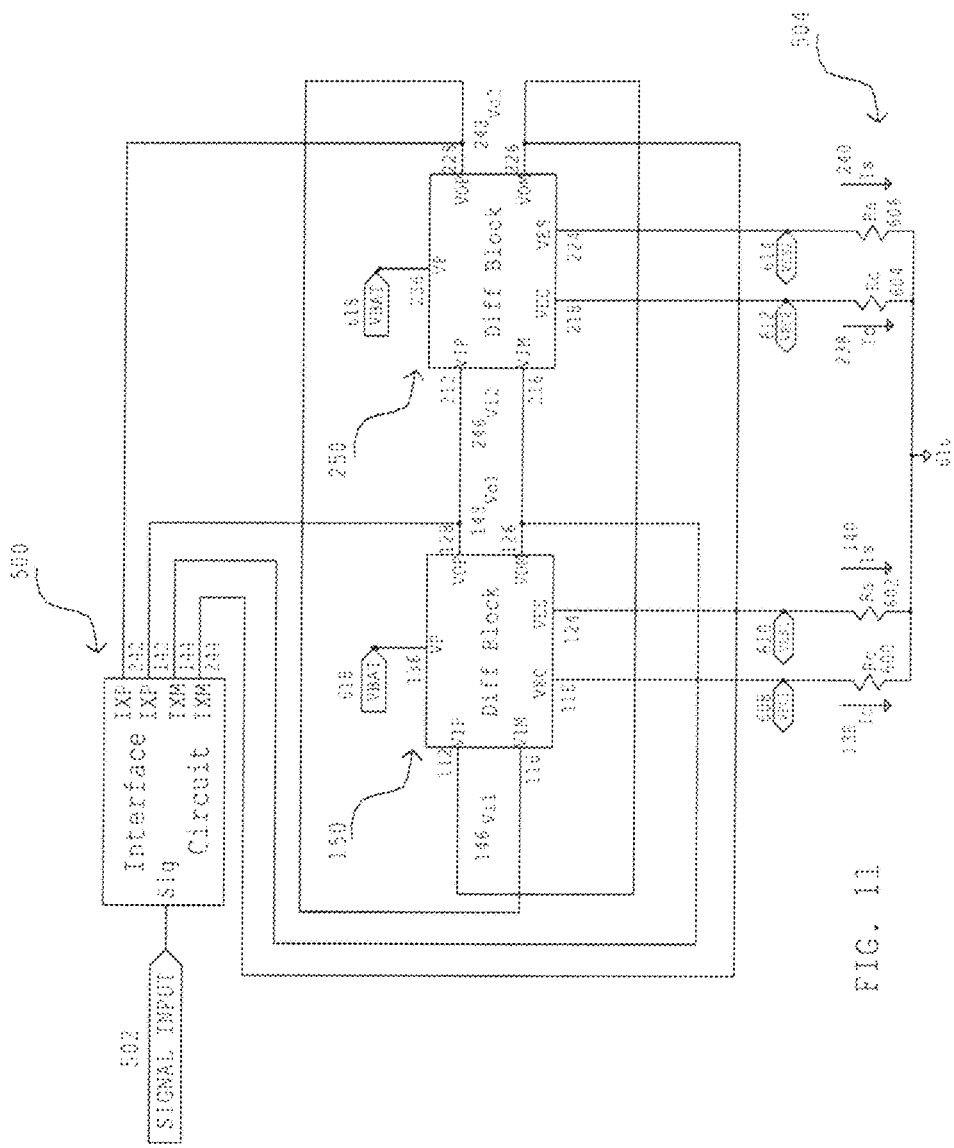
FIG. 11 shows an embodiment of the two-element system showing a discrete resistor approach for creating matched tail currents.

FIG. 11 illustrates an embodiment of FIG. 7 where the tail currents are created with use of resistors. In this simplified embodiment the four tail currents Ic 138, Is 140, Ic 238, and Is 240 are created by using resistors Rc 600, Rs 602, Rc 604, and Rs 606. More specifically, one end of resistor Rc 600 is connected to circuit stage 150 "Diff Block" node VEC 118. The other end of resistor Rc 600 is connected to ground 616. Similarly, one end of resistor Rs 602 is connected to node VES 124 of circuit stage 150. The other end of resistor Rs 602 is connected to ground 616. This connection scheme is repeated for the second stage 250 "Diff Block" where one end of resistor Rc 604 is connected to circuit stage 250 "Diff Block" node VEC 218. The other end of resistor Rc 604 is connected to ground 616. Finally, one end of resistor Rs 606 is connected to circuit stage 250 "Diff Block" node VES 224, and the other end of resistor Rs 606 is connected to ground 616. Also, this connection methodology may be extended to more than two circuit stages using additional resistors Rc and Rs for each node VEC and VES. Finally, a power supply or battery connection VBAT 618 is provided to node VP 136 of stage 150 and to node VP 236 of stage 250.

Figure 12:
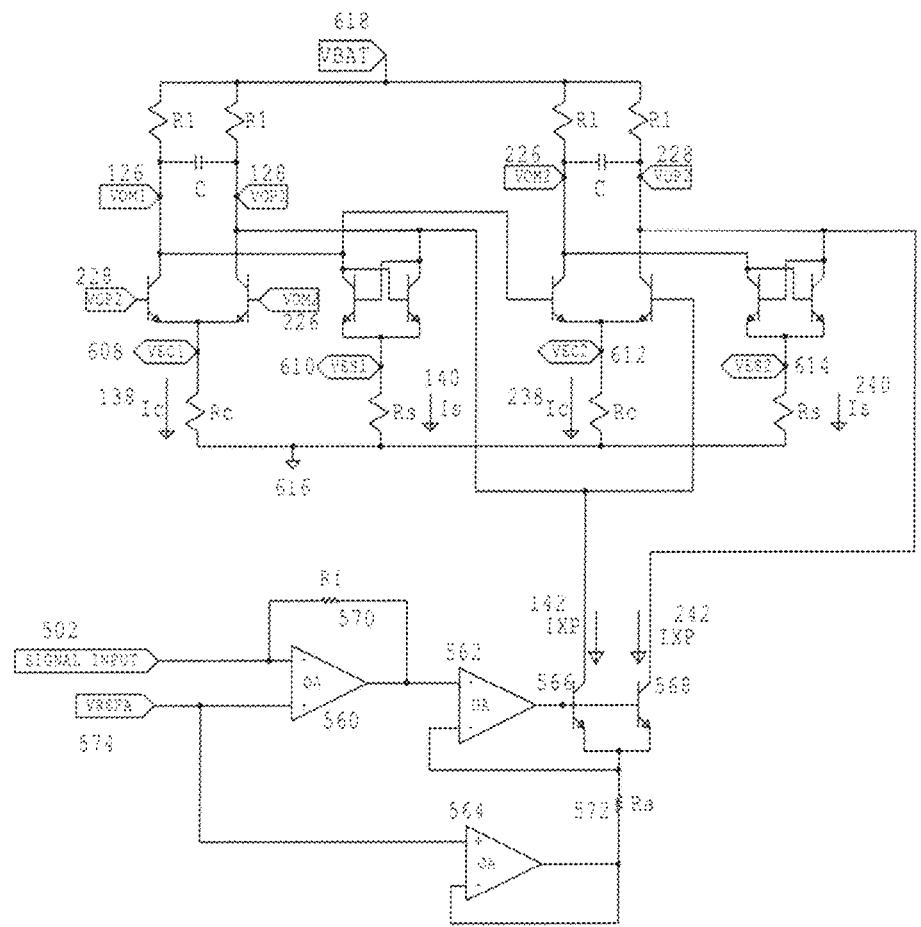
FIG. 12 shows an embodiment of the two-element system showing the transistor-level and operational amplifier-level schematics.

FIG. 12 shows an equivalent transistor-level schematic of the combined embodiments of FIG. 8, FIG. 10, and FIG. 11. This simplified embodiment uses the element transistor-level configuration of FIG. 8 where the supply rails VP become connected to common supply VBAT 618 with resistors Rc 138 through Rs 240 connected as in FIG. 11. The sense interface circuit of FIG. 10 is drawn at the bottom and connects IXP 142 to stage node VOP1 128 and connects IXP 242 to stage node VOP2 228. In this diagram, connections are shown with wires and with node labels. When a node label is repeated it indicates a wire connection. This applies specifically to nodes VOP2 228 and nodes VOM2 226 in which the wire connections are not shown. Instead, the connections for forming a feedback loop are implicit through the equivalent label, and a design engineer familiar with EDA design tools and schematic diagrams would recognize this methodology of connecting like nodes. The operational amplifiers OA 560, OA 562, and OA 564 are symbolic and the design engineer would follow standard practice for connecting supply and ground rails for operational amplifiers.

While the above disclosure describes possible ways of interconnecting an even number of blocks or stages with an input signal, this next section discusses possible ways of designing and operating such blocks in order to produce oscillatory behavior. In one embodiment, the goal may be to generate an oscillatory output signal whose fundamental frequency (f0) varies inversely with the magnitude of the variable and to be detected and/or measured input signal. The input signal, in turn, may be either a voltage signal or a current signal, and an important nonlinear transfer function becomes the frequency output relative to the signal input. Therefore, the first aspect of the design is to assure oscillation. Oscillations are guaranteed when the unperturbed, zero-signal-input, system is designed as an oscillator. While the connection algorithms automatically assure negative feedback, there are other variables, such as tail current and loading conditions, which are now addressed to assure the system has sufficient gain to behave as a differential ring oscillator. The design steps are discussed below with respect to the figures, and a design example, with specific component values, is provided to teach the engineer how to build a sense circuit capable of providing a frequency sensitive to low-level signal inputs.

In designing an oscillator, the engineer should understand the concepts of feedback theory and also understand how to use simulation tools such as HSPICE. A combination of theory and simulation are invaluable in predicting sense circuit performance and in studying how variables will affect the overall circuit performance. The concept discussed here regarding output and input signals finds application in the field of nonlinear dynamical systems. An input may be any type of signal input applied for example to both element A 102 and element B 104 of FIG. 1. The output may be observed at either element A 102 or element B 104.

Consider, in this regard, the circuit of FIG. 2, namely, the weakly bistable element with two differential pairs, where this is part of a larger system that functions as a ring oscillator. For proper operation and design, it is valuable to understand the variables of design. Here, the variables are the loads, comprised of Z1 130, Z1 132, and Z2 134, the tail currents which connect at terminals VEC 118 and VES 124, and the supply voltage VP 136. The designer should provide a supply voltage VP which allows enough voltage for adequate common-mode range, a standard electrical engineering concept. Also, this stage is intended to be part of a differential ring oscillator operated such that VIP 112 and VIM 116 are the non-inverting and inverting inputs, respectively, while VOP 128 and VOM 126 are the non-inverting and inverting stage outputs, respectively. In building the ring oscillator from several stages, each stage is designed to be matched, or identical. Mismatch tolerances should be studied with tools such as HSPICE and with experimentation.

Referring back to FIG. 3, the block diagram extension of FIG. 2, shows the additional currents Ic 138, Is 140, IXP 142, and IXM 144. Here Ic 138 and Is 140 are the tail currents which connect to VEC 118 and VES 124, respectively. These currents are design variables, and in one embodiment, Is 140 is larger in magnitude than Ic 138. The control currents IXP 142 and IXM 144 are currents which occur as a result of sensing a signal. These typically are scaled replicas of the sensed input, which may be a current or voltage. Each block or element of the complete system should be equivalent. So if one block receives just an IXP 142 input, then all blocks should receive just an IXP input of equivalent value. Thus, the system must be designed with "matched" currents. Matching errors should be studied and characterized as part of the design procedure, and circuit simulation allows the designer to study the effect of matching errors. Also, in normal operation, the circuit may be modeled with the simplified Ebers-Moll equations 152. In equations 152 the left-hand side of the equation, representing the linear term in Vo, has been written in terms of an inverse Laplace transform. In this way the impedances Z1 and Z2 may be expressed in the s-plane for convenience. The right-hand side of the equation, representing the nonlinear terms in Vo and Vi, is expressed in the time domain.

FIG. 4 and FIG. 5 represent the two-stage oscillator system operating as an oscillator with frequency dependent upon the control currents IXP 142 and IXM 144. In order to guarantee that the system will oscillate, one may use the Ebers Moll derivation giving a system of nonlinear equations similar to that of equation 252. An alternative electrical engineering approach would be to analyze the system as a feedback system and to use a control theory approach such as the Barkhausen stability criterion, which is a mathematical condition to determine when a linear electronic circuit will oscillate. This requires analyzing the small-signal gain of the differential stages and writing a transfer function for the control loop of interest. Either approach—the Ebers Moll nonlinear system analysis or the Barkhausen criterion—can be a starting point in the design. An HSPICE or similar computer-aided simulation analysis which uses more detailed models for transistors and for components would usually provide a better estimation of frequency and oscillator behavior.

Consider next and in this regard, the circuit of FIG. 6 which is a 2N generalization of FIG. 5 and it also is operated as an oscillator with matched currents. While there may be advantages to using more than two stages as shown in the embodiment of FIG. 6, the two-stage system offers the advantage of simplicity, including fewer stages and fewer components, and is explored here further as a preferred embodiment. Because this system is predicated upon matched elements and matched currents, the risk of mismatch errors from one element to the next is reduced when the design uses a minimum number of stages.

FIG. 7 shows the system-level block-diagram design of the two-stage sense-circuit. This operates as a system which senses the input signal 502 and then generates output signals Vo1 148 and Vo2 248 with frequency dependent upon the sense signal 502. The maximum frequency occurs when the input signal is zero such that the control currents IXP 142, IXP 242, IXM 144, and IXM 244 are zero. The frequency decreases monotonically with the control currents IXP 142, IXP 242, IXM 144, and IXM 244 until a DC condition is reached. For reliable circuit performance, the interface circuit 500 should therefore provide a scaled, predictable relationship between the sensed signal 502 and the control currents. In this way the output frequency will have a unique and predictable value as a function of the input sense signal 502. The tail currents of tail current generator 504 are design variables. Here tail currents Ic 138 and Ic 238 should be matched currents of equal value, to within design tolerance determined by simulation. Similarly, the tail currents Is 140 and Is 240 should be matched currents of equal value, to within design tolerance determined by simulation. Moreover, in one embodiment, the magnitude of Is is greater than the magnitude of Ic.

FIG. 8 shows a simplified embodiment of FIG. 2 where Z1 130, Z1 132, and Z2 134, have been replaced with passive components R1 530, R1 532, and C 534, respectively. Here the value of R1 530 and R1 532 is selected to be equal and such that the large-signal DC voltage drop across the resistor is small. This assures that the differential pairs will remain within common-mode range during normal operation. The capacitor C 534 is selected as a time-constant variable such that its value combined with R1 will represent a passive-load time constant. This time constant, in part, will affect the frequency of oscillation. The overall frequency is determined by the tail currents and the passive-load time constant, and HSPICE simulations are useful in predicting the frequency of the ring oscillator.

FIG. 9 shows one method for creating matched tail currents Ic 138 and Ic 238, and matched tail currents Is 140 and Is 240. In this active current source approach, the values Ic 138 and Ic 238 will be equal to half of VREFC 540 divided by Rc 548. Similarly, the values Is 140 and Is 240 will be equal to half of VREFS 550 divided by Rs 558. The values of VREFC 540 and VREFS 550 are constrained to voltage levels which allow the transistors to operate as current sources. The designer should verify correct operation through simulation. By way of example, suppose the desired value of Is 140 and Is 240 is 300 uA while the desired value of Ic 138 and Ic 238 is 200 uA. One approach is to use resistors Rc 548 and Rs 558 both equal to 1K and to select VREFC 540 and VREFS 550 equal to 0.4 V and 0.6 V, respectively.

FIG. 10 shows an interface-circuit method for creating matched control currents IXP 142 and IXP 242 from a current signal input 502. This interface circuit is operated as an interface circuit to scale an input current 502 by a scale factor equal to Rf 570 divided by Ra 572. The designer may determine by computer simulation the desired control values of IxP 142 and IXP 242 in order to realize a transfer function of frequency output versus control current level IXP. Then the sense level may be set by selecting an appropriate scale factor. For instance, suppose it is determined that based upon the tail currents an appropriate value of IXP 142 and IXP 242 is on the order of 10 uA; then a scale factor of 100 would be appropriate for sensing a current signal on the order of 100 nA. Say Ra 572 is selected as 10K (ohms), then Rf 570 would be 1 Meg (ohms). In this embodiment, the reference voltage VREFA 574 is selected as 0.5V and the sense input 502 is a current sink forcing the voltage across resistor Ra 572 to be positive. Therefore, this interface circuit is operated with the complete system as a monitor of a "sinked" current. Its function is to scale the sinked current by a predictable constant.

FIG. 11 again shows the system-level block-diagram design of the two-stage sense-circuit. However, in this embodiment the tail currents Ic 138, Ic 238, Is 140, and Is 240 are created by using matched or precision resistors Rc 600, Rc 604, Rs 602, and Rs 606, respectively. In this embodiment, suitable for a discrete-component PC board, the designer calculates Ic 138, Ic 238, Is 140, and Is 240 by knowing the large-signal voltages VEC1 608, VEC2 612, VES1 610, and VES2 614. If by design these voltages levels are approximately constant, then this procedure allows an alternative to using the current source of FIG. 9, and the tail currents are easily calculated using Ohm's law. For instance, Ic 138 is given by VEC1 608 divided by Rc 600.

FIG. 12 shows the two-stage transistor-level design of one embodiment with control currents IXP 142 and IXP 242 of FIG. 10. This also uses the passive tail-current approach of FIG. 11. There are no control currents IXM 144 and IXM 244 in this embodiment for sensing a sink current 502. This design uses the following component values: each Rc equal to 28K ohms, each Rs equal to 10K ohms, each capacitor C equal to 560 pF, each R1 equal to 500 ohms, a scale factor Rf/Ra equal to 150. The value Rf is selected to be 1.5 Meg ohm and Ra is thus equal to 10K ohms. A sink-directed current signal is sensed at sense input 502 while the output signal is measured across either capacitor C as VOP1 minus VOM1 or as VOP2 minus VOM2. A battery supply of 3.2 V is applied at VBAT, and VREFA is set to 0.5 V. Matched NPN bipolar transistors from a CA 3086 monolithically integrated chip are used to create the NPN differential pairs and matched currents.

Using the transistor HSPICE models from the CA 3086 datasheet and the parameters discussed above in FIG. 12, an HSPICE simulation gives a maximum frequency of 35.9 kHz when the control currents IXP are zero. The simulation also calculates the tail currents: tail-current value Ic equals 92 uA, and tail-current value Is equals 255 uA.

Working Example: A complete circuit as shown in FIG. 12 has been tested on a proto-board for evaluation; and additionally a corresponding HSPICE simulation were found to correctly predict the maximum (zero control current) frequency to within 10 percent. Error between simulation and breadboard results are attributed to mismatch errors of matched components including mismatch among the differential pairs. Other sources of error may be parasitic board capacitance, probe capacitance, and voltage errors relating to using an unregulated power source. To attain consistent and predictable circuit performance the designer could use a regulated power supply or use a voltage regulator to regulate the supply voltage labeled as VBAT. Also, the system design is not limited to using a protoboard; and the designer may wish to use a PC-board or a monolithic integrated solution to fabricate the sense circuit.

FIG. 13 shows the simulated differential output voltages VO1 and VO2 of the circuit in FIG. 12. Here VO1 is defined as VOP1 128 minus VOM1 126 while VO2 is defined as VOP2 228 minus VOM2 226. These HSPICE generated waveforms substantially agree with the experimental waveforms of the working example.

FIG. 14 shows the simulated output response to a current sink signal at sense input 502. In this simulated example, the sensed current is ramped from zero to 75 nA over the indicated time interval and it may be seen by measuring pulse width that the fundamental frequency varies inversely with sense current. The interface circuit scale factor, determined by Rf 570 and Ra 572, has been adjusted in this example to force the frequency to be zero (no oscillation) for values of sense current greater than 75 nA and to have maximum transfer gain when the sense current reaches 10 nA. Here, transfer gain refers to the magnitude of the transfer function of output frequency with respect to sense current input. By forcing this characteristic, the sense circuit is highly sensitive and has maximum transfer gain, when the sink current signal is between 10 nA and 75 nA. It is within the contemplation of the present disclosure to otherwise vary the control parameters to obtain desired sensitivity and oscillation cut-off at other values.

FIG. 13 and FIG. 14 as described above therefore provide insight into how a person may elect to operate the sense circuit in view of the present teachings. In the simulated examples of FIG. 13 and FIG. 14, a to-be-sensed current signal of just several nano-amps (nA) may cause the output signals VO1 and VO2 of FIG. 12 to change (e.g., decrease) substantially and thus distinguishably. The above and merely exemplary and not limiting design provides an observable change of fundamental output frequency based upon the input signal at sense input 502. The shape of the waveform also changes as seen in FIG. 14. It is within the contemplation of the disclosure to change design variables, such as tail current (values Is and Ic) and passive load (values Z1 and Z2), in order to realize different frequency transfer characteristics. For instance, it is possible, in theory, to vary Is and Ic to change the zero-input frequency to a range of 100 kHz and to change the sensed current level to less than 1 nA. Another variable is the interface circuit gain, and this too could be adjusted to shift the sensed-current level.

Figure 15:
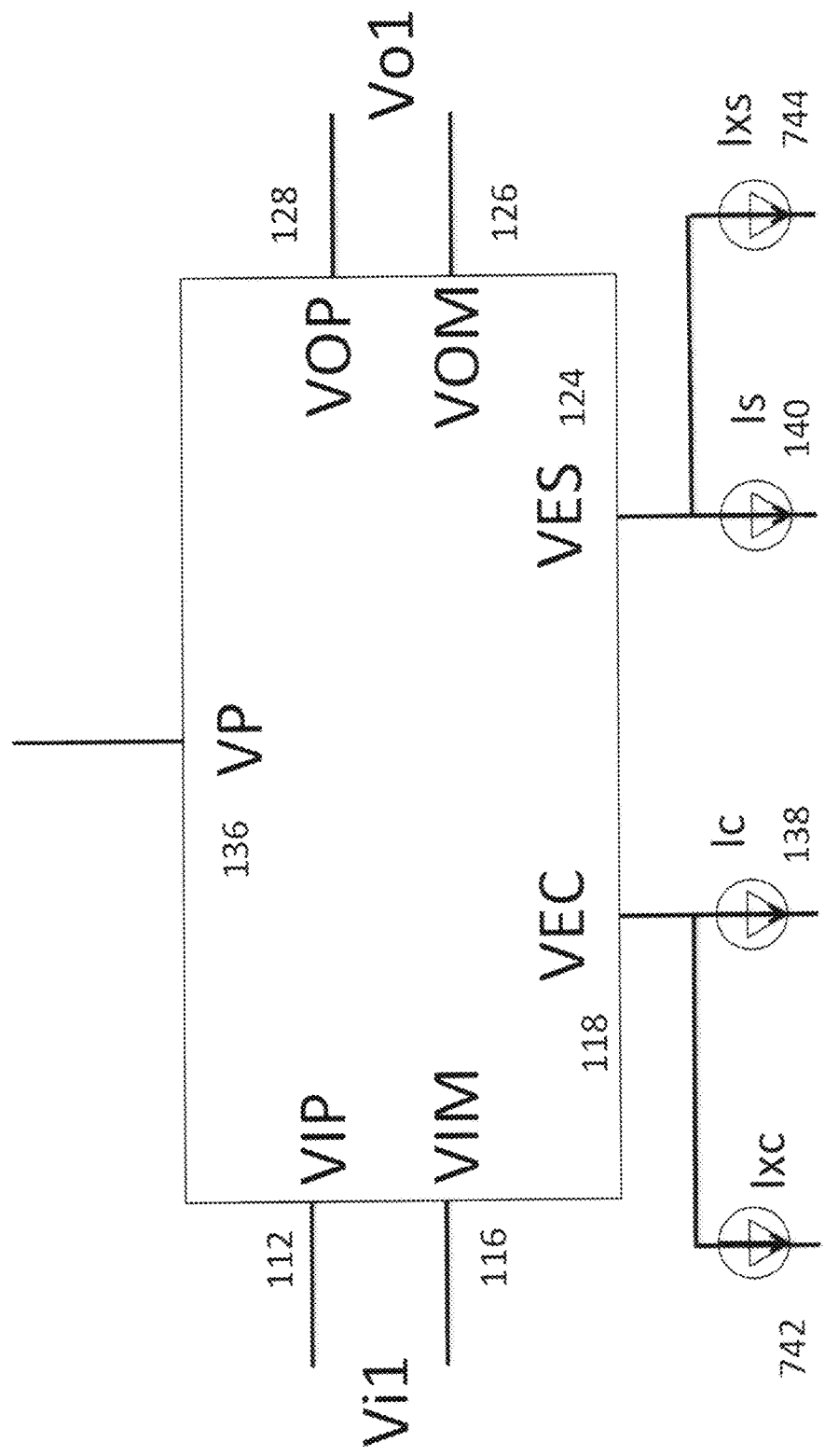
FIG. 15 shows an alternative embodiment of the sense current block interfaced with the two element system.

The present disclosure is to be taken as illustrative rather than as limiting the scope, nature, or spirit of the subject matter claimed below. Numerous modifications and variations will become apparent to those skilled in the art after studying the disclosure, including use of equivalent functional and/or structural substitutes for elements described herein, use of equivalent functional couplings for couplings described herein, and/or use of equivalent functional steps for steps described herein. Such insubstantial variations are to be considered within the scope of what is contemplated here. Moreover, if plural examples are given for specific means, or steps, and extrapolation between and/or beyond such given examples is obvious in view of the present disclosure, then the disclosure is to be deemed as effectively disclosing and thus covering at least such extrapolations. As an example, FIG. 15 shows an alternative way to connecting the interface circuit to the diff-pair unit. In this case, instead of connecting the interface circuit to the diff-pair collectors, one can connect them directly to the diff-pair emitters and modulate the frequency.

More specifically, the present disclosure provides an oscillatory ring or loop that includes at least two weakly bistable (wb) differential amplifiers such as the one shown in FIG. 2 where the wb-differential amplifiers are biased such that at the ring (loop) will be in a first oscillatory mode (or not oscillating) when no weak tipping signal is applied to one or more of the at least two wb-differential amplifiers and such that a weak tipping signal (e.g., one in a range of about 2 nA to 75 nA as shown in FIG. 14), when applied to at least one of the two or more wb-differential amplifiers will discernibly shift the loop into a different oscillatory mode (or into a not oscillating mode) so that the discernible shift indicates the detection of the weak tipping signal. Although the exemplary wb-differential amplifier of FIG. 2 uses NPN bipolar transistors operating in their nonlinear and near threshold regions, it is within the contemplation of the present disclosure to instead use PNP transistors, JFET transistors (of P or N channel type), OnFETs (of P or N channel type), other forms of IGFETs (Insulated Gated Field effect transistors), Darlington pairs and/or combinations of IGFETs and bipolar transistors for obtaining similar functionalities from such other active devices. While one embodiment uses just two stages each having only 4 transistors, the concepts provided here may be generalized to using any even number of such stages where the overall feedback coupling allows for oscillations and a weak tipping signal can tip the loop or ring from one oscillatory mode to a distinguishable second oscillatory mode (or to a non-oscillatory mode as shown for example at the right end of FIG. 14).

Figure 16A:
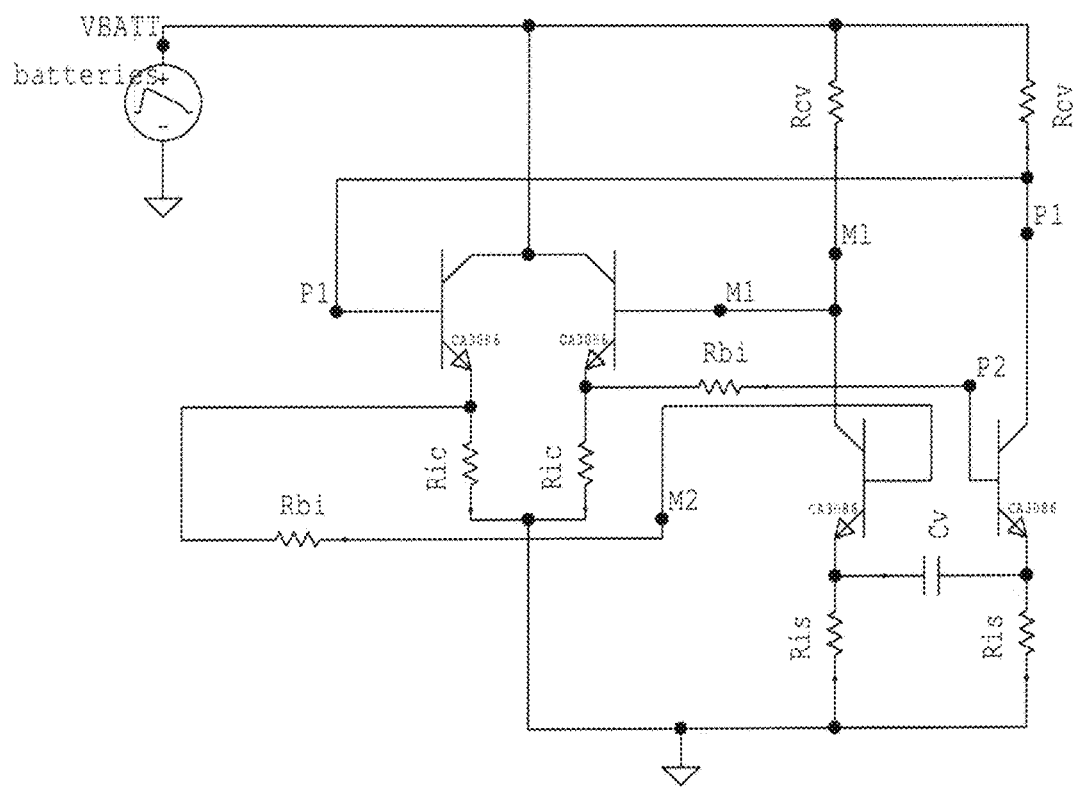
FIG. 16A shows an embodiment of the one element system.
Figure 16B:
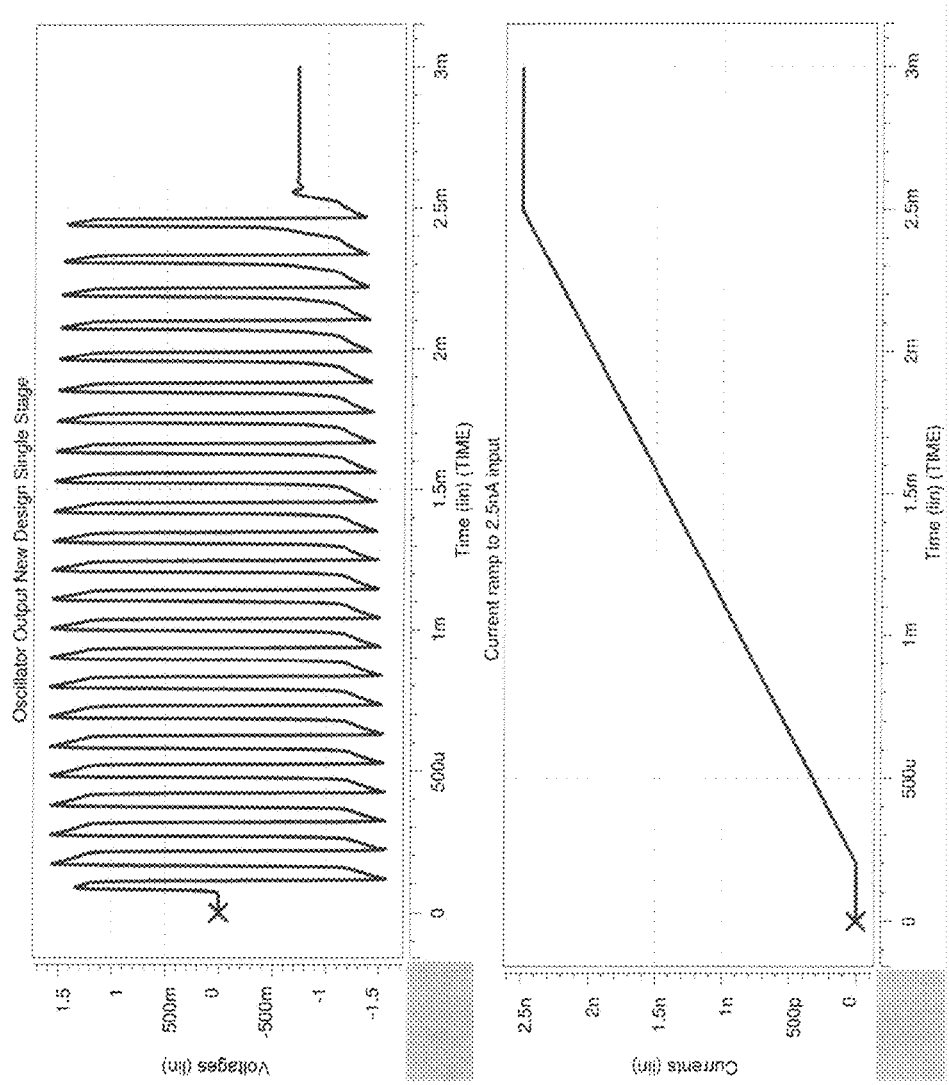
FIG. 16B shows a plot produced from an HSPICE simulation result showing the differential output voltages when a behavior-tipping and weak sense current is applied as an increasing ramp over time.

FIG. 16A depicts a stage of a one-element oscillatory system that may be operated in accordance with the present disclosure. As shown in FIGS. 16A and 16B, one stage with oscillation can be perturbed toward a non-oscillatory mode.

Therefore, one, two or any even number of stages can be used to sense weak signals. Previously, it went unnoticed that the oscillation regime transitions into a non-oscillatory regime, therefore exhibiting a bifurcation process due to a non-linear process, even with an even-number of stage loops (e.g., a two-stage loop shown in FIG. 1A). U.S. Pat. No. 8,212,569 to In et al. and entitled "Coupled bi-stable circuit for ultra-sensitive electric field sensing utilizing differential transistor pairs" and U.S. Pat. No. 7,420,366 to In et al. and entitled "Coupled nonlinear sensor system," for example, describe systems with odd-number of oscillators based on general transistor(s) but do not contemplate even-numbered or single-numbered oscillators. The inventive concept disclosed herein is based on the discovery that the transition between the oscillation and non-oscillatory regimes can be achieved with even-number of stage loops, and in fact, can even be achieved with a one-stage loop as shown in FIG. 16A and FIG. 16B.

Furthermore, the input sense circuit can be further modified to inject voltage input rather than current input into one or multistage system such that one can sense the voltage with which many electrically excitable biophysical measurements can be applied.

If any disclosures are incorporated herein by reference and such incorporated disclosures conflict in part or whole with the present disclosure, then to the extent of conflict, and/or broader disclosure, and/or broader definition of terms, the present disclosure controls. If such incorporated disclosures conflict in part or whole with one another, then to the extent of conflict, the later-dated disclosure controls.

Unless expressly stated otherwise herein, ordinary terms have their corresponding ordinary meanings within the respective contexts of their presentations, and ordinary terms of art have their corresponding regular meanings within the relevant technical arts and within the respective contexts of their presentations herein. Descriptions above regarding related technologies are not admissions that the technologies or possible relations between them were appreciated by artisans of ordinary skill in the areas of endeavor to which the present disclosure most closely pertains.

Given the above disclosure of general concepts and specific embodiments, the scope of protection sought is to be defined by the claims appended hereto and their equivalents. The inventive concept(s) disclosed herein as taken alone or in various combinations (including but not limited to embodiments of FIGS. 1A-16B) are intended to be claimed. The issued claims are not to be taken as limiting Applicant's right to claim disclosed, but not yet literally claimed, subject matter. A general claim to all here disclosed and inventive matter is hereby made.

What is claimed is:

1. A signal sensing device comprising:
    a first weakly bistable differential amplifier provided as a stage within an oscillatory loop that is configured to sustain oscillations, wherein the oscillatory loop has one or an even number of stages;
    a second weakly bistable differential amplifier also provided as a stage within the oscillatory loop;
    a behavior perturbing coupling connected to at least one of the first and second weakly bistable differential amplifiers and operative to introduce into the connected-to amplifier a behavior tipping signal such that the behavior tipping signal alters the oscillatory behavior of the oscillatory loop in a distinguishable way; and
    an interface circuit block comprising a resistor and a shunt feedback resistor coupled to receive a current signal, whereby in response to the current signal the interface circuit block provides the behavior tipping signal in proportion to the current signal and a scale factor, the scale factor determined, at least in part, by a ratio of a resistance of the shunt feedback resistor with a resistance of the resistor.

2. The signal sensing device of claim 1, wherein the behavior perturbing coupling is configured to alter the oscillatory behavior of the oscillatory loop, even if the behavior tipping signal is weaker than an oscillation of the oscillatory loop.

3. The signal sensing device of claim 1, wherein:
    the behavior tipping signal is a current signal of a magnitude less than 100 nanoAmperes (100 nA).

4. The signal sensing device of claim 1 wherein the behavior tipping signal is a current signal of a magnitude less than 25 nA.

5. The signal sensing device of claim 1 wherein:
    the oscillatory loop is a two-stage loop having no more than the first and second weakly bistable differential amplifiers as its stages.

6. The signal sensing device of claim 1 wherein each of the first and second weakly bistable differential amplifiers comprises:
    a differential load portion having at least first and second matched impedances both connected to a first current splitting node;
    a differential amplifier portion having first and second active devices that match each other, each of the active devices being coupled to a respective one of the first and second impedances such that if the first and second active devices are in matched states they will draw equal currents from their respective ones of the first and second impedances;
    a latch portion having third and fourth active devices that match each other, each of the third and fourth active devices being coupled to a respective one of the first and second impedances, the latch portion being configured to urge the differential load portion into an imbalanced current draw state wherein currents drawn through the first and second matched impedances are not equal.

7. The signal sensing device of claim 6 wherein the first and second active devices each includes a transistor having a nonlinear region of operation in which the transistor provides a high gain transfer function greater than that of a linear region of operation for the same transistor, and wherein the signal sensing device further comprises:
    an amplifier biasing portion configured to urge each of the first and second active devices into a normally biased mode in which the transistor operates in its nonlinear region of operation.

8. The signal sensing device of claim 7 further comprising:
    a latch biasing portion configured to urge each of the third and fourth active devices into a normally biased mode in which the transistor operates in a corresponding nonlinear region of operation of its operational characteristics, the corresponding nonlinear region of operation providing a high gain transfer function greater than that of a linear region of operation the same active device.

9. The signal sensing device of claim 7 wherein the each transistor is at least one of:
    a NPN bipolar transistor;
    a PNP bipolar transistor;
    a Junction Field Effect Transistor (JFET); and
    an Insulated Gate Field Effect Transistor (IGFET);
    a Darlington pair connected combination of bipolar transistors;
    a BiMOS transistor; and
    a MOSFET transistor.

10. A method of detecting a weak signal, the method comprising:
    providing an oscillatory loop that sustains oscillations, wherein the loop includes one or an even number of stages, and wherein the oscillatory loop includes a first weakly bistable differential amplifier and a second weakly bistable differential amplifier;
    connecting at least one of the first and second weakly bistable differential amplifiers to a behavior perturbing coupling which is operative to introduce into the connected-to amplifier a behavior tipping signal where, even if the behavior tipping signal is weaker than an oscillation of the multistage oscillatory loop along the time axis, the behavior tipping signal alters the oscillatory behavior of the multistage oscillatory loop in a distinguishable way; and
    providing a signal derived from the weak signal to an interface circuit block comprising a resistor and a shunt feedback resistor and to the at least one of the first and second weakly bistable differential amplifiers as the behavior tipping signal, wherein the behavior tipping signal is proportional to the signal derived from the weak signal and a scale factor that is determined, at least in part, by a ratio of a resistance of the shunt feedback resistor and a resistance of the resistor.

11. The method of claim 10 wherein:
    the behavior tipping signal is a current signal of a magnitude less than 100 nanoAmperes (100 nA).

* * * * *